United States Patent [19]
Logothetis et al.

[11] Patent Number: 5,783,153
[45] Date of Patent: Jul. 21, 1998

[54] METAL OXIDE OXYGEN SENSORS BASED ON PHASE TRANSFORMATION

[75] Inventors: Eleftherios Miltiadis Logothetis, Birmingham; Richard E. Soltis, Saline, both of Mich.

[73] Assignee: Ford Global Technologies, Inc., Dearborn, Mich.

[21] Appl. No.: 905,372

[22] Filed: Aug. 4, 1997

[51] Int. Cl.⁶ .................................................. G01N 27/12
[52] U.S. Cl. ........................... 422/83; 422/90; 422/91; 422/94; 422/98; 73/23.32
[58] Field of Search ...................... 422/90, 98, 88, 422/91, 83, 94; 436/137; 73/23.32; 338/34; 356/432

[56] References Cited

U.S. PATENT DOCUMENTS

| | | |
|---|---|---|
| 3,933,028 | 1/1976 | Laud et al. . |
| 4,208,265 | 6/1980 | Hori et al. . |
| 4,209,378 | 6/1980 | Schinohara et al. . |
| 4,228,128 | 10/1980 | Esper et al. . |
| 4,253,931 | 3/1981 | Gold et al. . |
| 4,320,378 | 3/1982 | Taniguchi et al. . |
| 4,328,295 | 5/1982 | Tanaka et al. . |
| 4,328,296 | 5/1982 | Tanaka et al. . |
| 4,351,182 | 9/1982 | Schmidberger . |
| 4,535,316 | 8/1985 | Wertheimer et al. . |
| 4,574,264 | 3/1986 | Takahashi et al. . |
| 4,764,343 | 8/1988 | Nyberg .................................. 436/137 |
| 4,824,549 | 4/1989 | Hamada et al. . |
| 5,017,340 | 5/1991 | Pribat et al. . |
| 5,238,549 | 8/1993 | Makino et al. . |
| 5,372,838 | 12/1994 | Aoki et al. . |
| 5,384,030 | 1/1995 | Duce et al. . |
| 5,397,541 | 3/1995 | Post . |
| 5,417,061 | 5/1995 | Maeda et al. . |
| 5,443,711 | 8/1995 | Kojima et al. . |
| 5,445,796 | 8/1995 | Mori . |
| 5,480,535 | 1/1996 | Kondo et al. . |
| 5,492,612 | 2/1996 | Kennard, III et al. . |
| 5,510,013 | 4/1996 | Hippe et al. . |
| 5,520,787 | 5/1996 | Hanagan et al. . |
| 5,538,612 | 7/1996 | Kojima et al. . |

OTHER PUBLICATIONS

E. M. Logothetis, "ZrO₂ oxygen sensors in automotive applications," 1981, The American Ceramic Society.

E. M. Logothetis, "Resistive–Type Exhaust Gas Sensors," American Ceramic Society.

E. M. Logothetis, "Air–to–Fuel Sensors Based on Oxygen Pumping" 1987 pp. 1058–1073, Reprinted form the Ceramic Engineering and Science Proceedings, vol. 8, No. 9–10.

(List continued on next page.)

*Primary Examiner*—Jeffrey Snay
*Attorney, Agent, or Firm*—Lorraine S. Melotik

[57] ABSTRACT

The invention is a sensing method and an oxygen sensor for detecting a change of oxygen partial pressure in an ambient atmosphere. The sensor includes a sensing material selected from metal or its oxides which, when at an elevated temperature and exposed to a gas containing a changing partial pressures of oxygen, is capable of changing from one metal or metal oxide phase to another such oxide phase and vice versa. Associated with such phase change is a change in a measurable physical property of the material. Heating elements, connectable to a power source, able to maintain a temperature gradient across said sensing material are necessary to maintain the material, during active sensing operation, in at least two of the phases defining a boundary line therebetween which is generally perpendicular to the longitudinal axis of the temperature gradient. The boundary line traverses longitudinally along the axis in response to changes in the oxygen partial pressure of the ambient atmosphere to which the sensing material is exposed. The sensor also includes a device for furnishing an output signal in response to the traversal of the boundary line across a fixed detecting location of the sensing material. Hence, the invention senses the passage of the boundary line at some specific location in the material to detect a specific $P_{O_2,c}$.

18 Claims, 3 Drawing Sheets

OTHER PUBLICATIONS

G. L. Beaudoin, K. R. Laud, E. M. Logothetis, A. H. Meitzler, and K. Park, "CoO Sensors for Measurement and Control of Exhaust from Lean–Burn Engines," 760312, Engineering & Research Staff, Ford Motor Company.

Kwansuh Park and E. M. Logothetis, "Oxygen Sensing with $Co_{1-x}Mg_xO$ Ceramics," 1977, pp. 1443–1446, Reprinted from Journal of the Electrochemical Society, vol. 124, No. 9.

Michael L. Post, Brian W. Sanders and P. Kennepohl, "Thin film of non–stoichiometric perovskites as potential oxygen sensors," 1993, p. 272–275, Sensors and Actuators B, 13–14.

METAL OXIDE OXYGEN SENSORS BASED ON PHASE TRANSFORMATION

Reference is made to related application Ser. No. 08/905,892 titled "High Sensitivity Phase-Transformations-Based Oxygen Sensors for Proportional Control" concurrently filed with this application and having the same inventorship.

FIELD OF THE INVENTION

This invention is directed to oxygen sensors which detect changes in oxygen partial pressure in an ambient atmosphere based on phase changes of a material, e.g., cobalt oxide which can change from one phase of cobalt oxide, $Co_3O_4$, to another, CoO.

BACKGROUND OF THE INVENTION

Oxygen sensors have received widespread attention particularly for applications like combustion control, process control, and medical applications. In the automotive area, oxygen sensors are used to control the Air-to-Fuel Ratio (A/F) of internal combustion engines. The great majority of present day automobiles employ an electrochemical-type oxygen sensor to control the A/F ratio. Generally this ratio is controlled at the stoichiometric value, about 14.4–14.7, where the so-called three-way catalysts have the greatest efficiency for eliminating regulated emissions (hydrocarbons, carbon monoxide, and oxides of nitrogen) from the exhaust gas. A conventional automotive oxygen sensor, sometimes called a lambda sensor, includes an oxygen-ion-conducting solid electrolyte, generally $ZrO_2$, in the form of a thimble with porous platinum electrodes deposited on the outside and the inside surfaces of the thimble. The inside of the thimble is exposed to ambient air as a reference atmosphere, whereas the outside of the thimble is exposed to the exhaust gas. When the thimble is heated (e.g. temperatures higher than 300° C.) and there is a difference in the oxygen partial pressures $P_{O2}$ between the two sides of the $ZrO_2$ thimble, an electromotive force (emf) is generated between the two Pt electrodes with a value given by the Nernst equation: $emf=(RT/kT) \ln(P_{O2}, exh/P_{O2}, air)$.

When the sensor is placed in the exhaust gas of a vehicle, and the A/F is varied, the sensor emf shows a large and abrupt change at the stoichiometric A/F value as shown in FIG. 1. The reason is that the thermodynamic equilibrium oxygen partial pressure in the exhaust gas changes by many orders of magnitude at the stoichiometric A/F ratio. Away from stoichiometry, the emf varies only slowly with A/F because the partial oxygen pressure also changes only slowly with A/F.

Another type of a high temperature oxygen sensor useful in automotive applications is a resistive-type sensor based on $TiO_2$. At elevated temperatures, the electrical resistivity of metal oxides like $TiO_2$, $SrTiO_3$ and CoO depends on the oxygen partial pressure $P_{O2}$ in the ambient gas atmosphere. This dependence is, however, generally weak. For example, for $TiO_3$, $SrTiO_3$ and CoO, this dependence is only a positive or negative ¼ to ⅙ power dependence. In spite of their weak $P_{O2}$ sensitivity, $TiO_2$ sensors are useful for stoichiometric A/F control because they also exhibit a large and abrupt electrical resistance change at the stoichiometric A/F value as the result of the large change in exhaust gas $P_{O2}$ near stoichiometry.

In addition to stoichiometric oxygen sensors, there is a growing need for oxygen sensors that can measure A/F away from stoichiometry, in particular in the lean A/F region where excess oxygen is employed. These A/F ratios are often 19–40. Many engines are being modified for lean operation because of the fuel economy advantages which can be achieved. These sensors must have high $P_{O2}$ sensitivity because the oxygen partial pressure in the exhaust gas does not change appreciably with A/F in this region. As discussed above, the conventional $ZrO_2$ lambda sensor and the resistive-type sensors previously mentioned have very limited sensing ability away from stoichiometry. In addition the resistive-type sensor generally have a strong dependence on temperature.

On the other hand, another type of sensor, i.e., a $ZrO_2$ based sensor operating in the oxygen pumping mode, has much higher sensitivity (e.g. 1st-power $P_{O2}$ dependence) away from stoichiometry. Examples of this type of sensor are the Universal Exhaust Gas Oxygen Sensor (UEGO) and the Lean Exhaust Gas Oxygen Sensor (LEGO) based on two $ZrO_2$ cells. These sensors are structurally complex and consequently expensive to manufacture, which limits their widespread commercialization. As a result, efforts are continuing to develop a simple sensor having high oxygen sensitivity for A/F measurement away from stoichiometry.

It is known that some metal oxides change to another metal oxide phase when the temperature or the $P_{O2}$ are changed appropriately. For example, at a given temperature, CoO is stable at low $P_{O2}$, but at higher $P_{O2}$, it transforms to $Co_3O_4$ as shown in FIG. 2. Such metal-oxide to metal-oxide phase transitions are also generally accompanied by large changes in their electrical resistivity which can make these materials useful for oxygen sensors. In the case of cobalt oxide, the resistance decreases by almost two orders of magnitude when CoO changes to $Co_3O_4$. FIG. 3 shows results of the large stepwise changes in the resistance of a porous cobalt oxide ceramic as a function of $P_{O2}$ at several temperatures associated with the phase change from CoO to $Co_3O_4$.

The resistivity of $Co_3O_4$ is independent of $P_{O2}$, whereas the resistivity of CoO decreases with increasing $P_{O2}$ according to the relationship $R=A \exp(E/kT)(P_{O2})^{-1/4}$. This property of CoO has been utilized in fabricating oxygen sensors as disclosed by G. L. Beaudoin et al., SAE Paper No. 760312, Feb. 23, 1976 and U.S. Pat. No. 3,933,028 to K. R. Laud et al. For example, if the temperature of the material is kept at some temperature in the range 900°–1000° C., the resistance of CoO can be used to measure changes in the $P_{O2}$ of ambient air, or changes in the A/F ratio of internal combustion engines, e.g., gasoline and diesel, in the lean region. This type of prior art sensor consisted of a porous CoO ceramic with two Pt wires embedded into the ceramic, and inserted into a miniature cylindrical furnace to maintain the temperature of the CoO element at a constant high temperature. FIG. 4 shows the resistance of such a CoO ceramic as a function of the A/F ratio of an internal combustion engine in the lean region from A/F=14.8 to A/F=18. The oxygen sensitivity of this sensor, however, is seen from FIG. 4 to be low. That is, the resistance changes by a factor of only about 2 when the oxygen partial pressure in the exhaust gas charges from about $5\times10_{-3}$ atm. (A/F=14.8) to about $6\times10^{-2}$ atm. (A/F=18).

The large change in the resistance of a ceramic due to the conversion of the material from one oxide phase to the other, however, may be used to make a more sensitive oxygen sensor. And the oxygen partial pressure in the ambient gas can be determined, for example, by ramping the sample temperature between two appropriate values and monitoring the temperature for which the resistance changes by a large amount and then using the phase diagram of FIG. 2 to determine the ambient $P_{O2}$. When one wants to use this sensor to control the oxygen partial pressure at a specific value $P_{O2,c}$, the temperature of the sample is kept constant at the value $T_c$ for which the sample converts from one oxide phase to the other at that specific oxygen partial pressure.

U.S. Pat. No. 4,351,182 to Schmidberger discloses a sensor for monitoring the oxygen content in oxygen rich exhaust gases from furnaces based on material phase transformations, more particularly from metal to metal oxide and vice versa. The oxygen sensitive material is a palladium layer maintained at a specific high temperature, e.g. 700° C., whereby palladium metal (Pd) changes phase to palladium oxide (PdO) when the oxygen partial pressure exceeds a specific "critical" value, $P_{O2,c}$. It is disclosed that the phase change from Pd to PdO, and back, causes a change in the material's conductivity by a factor of about 20 which is used to provide a sensor output signal.

Phase transitions from a metal to metal oxide, or from a metal oxide to another metal oxide are known to be generally accompanied by significant hysteresis unless the $P_{O2}$ is changed to a value substantially larger (or smaller) than $P_{O2,c}$. Hysteresis is related to the time that it takes for the material to change from one phase to another and is believed to be associated with a necessary nucleation process, i.e., formation of critical size nuclei of the new phase. The presence of hysteresis in phase transformation type sensors would negatively impact their usefulness since they would have relatively long response time.

The present invention overcomes the deficiencies of prior sensors and provides an oxygen sensor useful for automotive applications having excellent sensitivity and response time in a variety of A/F ratios, including lean-burn engines.

SUMMARY OF THE INVENTION

The present invention is a sensor for detecting a change of oxygen partial pressure in an ambient atmosphere. The sensor includes a sensing material which is selected from metal or its oxides and which, when at an elevated temperature and exposed to a gas containing a changing partial pressures of oxygen, is capable of changing from one metal or metal oxide phase to another such oxide phase and vice versa and associated therewith a change in a measurable physical property thereof. The sensor also includes a heating means connectable to a power source able to maintain a temperature gradient across the sensing material whereby the material exists, during active sensing operation, in at least two of said phases defining a boundary line therebetween generally perpendicular to the axis of the temperature gradient. The boundary line traverses longitudinally along the axis in response to changes in the oxygen partial pressure of the ambient atmosphere. Exemplary of these measurable physical properties are electrical resistivity, optical absorption, and mass.

The sensor also includes a means for furnishing an output signal in response to the traversal of the boundary line across a fixed detecting location of the sensing material. For example, when such means is related to detecting changes in electrical resistance associated with the boundary line traversal across a fixed detecting location, the means may involve spaced apart electrical means at the detecting location for measuring changes in electrical resistance (or alternately conductivity) of the material therebetween, the means being located within the sensing material or on the same or opposing sides of the sensing material surfaces and optimally being generally centrally located along the axis of the temperature gradient.

In another embodiment, the present invention is a method for detecting a change of oxygen partial pressure in an ambient atmosphere. This method includes the steps of locating a sensor, as described above, in contact with an ambient atmosphere containing oxygen. The sensing material is present according to the method in at least two phases, during active sensing operation, defining a boundary line therebetween, the phases being selected from metal and oxides thereof wherein at least one of the phases is an oxide phase as defined above. The method further comprises the steps of maintaining a temperature gradient across the sensing material so as to maintain the material, during active sensing operation, in at least two phases defining a boundary line therebetween generally perpendicular to the longitudinal axis of the temperature gradient wherein the boundary line traverses longitudinally along this axis in response to changes in the oxygen partial pressure of the ambient atmosphere, and furnishing an output signal in response to traversal of the boundary line across a fixed detecting location of the sensing material. Preferably, the furnishing step comprises furnishing such signal based on detecting a change of electric resistance of the material at the fixed detecting location between spaced apart electrical means affixed within or on the surface of the same or opposing sides of the sensing material. The fixed detecting location of the sensing material optimally is generally centrally located along the axis of the temperature gradient. The output signal would thus be furnished in response to the traversal of the boundary along the longitudinal axis of the temperature gradient in a region between the spaced apart electrical means.

The oxygen sensor of the present invention advantageously provides a relatively low cost sensor with excellent sensitivity and response time. In addition, the sensor is much less complex to fabricate than many present sensors because it does not need the high quality seal between exhaust gas and air.

DETAILED DESCRIPTION OF THE PREFERRED EMBODIMENTS

The oxygen sensor disclosed herein is useful for detecting a change of oxygen partial pressure in an ambient atmosphere. It includes a sensing material which is selected from metal or its oxides which, when at an elevated temperature and exposed to a gas containing a changing partial pressures of oxygen, is capable of changing from one metal or metal oxide phase to another such oxide phase and vice versa. Associated with such phase changes are changes in a measurable physical property, such as electrical resistance.

The sensing material may be a single metal, oxide thereof, or a compound of two or more metals or oxides thereof. It may also be a mixture of such materials. Preferred metals include, but are not limited to, metals like copper, palladium, indium, ruthenium, and rhodium; 3d transition metals; and rare earth elements. Exemplary of such 3d transition metals are titanium, vanadium, chromium, manganese, iron, cobalt, and nickel to name a few. Exemplary rare earth elements include La, Ce, Pr, Ni, Sm, Eu, Gd, Er etc. The sensing material may be a ternary and higher order compounds of the above metals with other elements like alkaline earth elements, e.g., calcium, strontium, or magnesium or oxide thereof such as CoMgO and SrFeO, or such compounds formed with rare earth elements such as $La_2CuO_3$, $La_2CuO_3$, $PrFeO_3$. Still other ternary and higher order compounds or oxides thereof of rare earth elements with other elements, e.g., $Y_mBa_nCu_kO_x$ may also be employed herein. Mixtures of any of these materials would also be useful. The sensing materials useful in this invention are not limited to those listed above but may be any metal material or oxide thereof which undergoes a phase change in response to changing partial oxygen pressures and has associated therewith a change in a measurable physical property.

Figure 2:
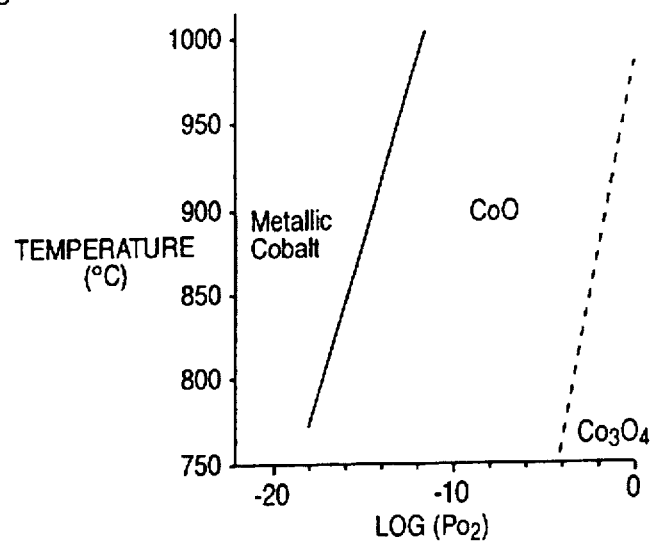
FIG. 2 is a $P_{O2}$ vs. T graph of the phase diagram for the Co-O system.
Figure 3:
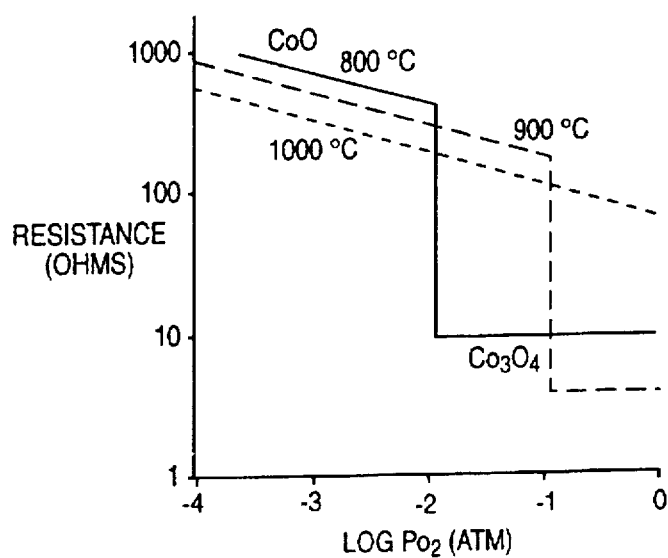
FIG. 3 is a graph showing the stepwise change in resistance of a cobalt oxide ceramic sample as a function of $P_{O2}$ at several temperatures due to the phase change from CoO to $Co_3O_4$.
Figure 4:
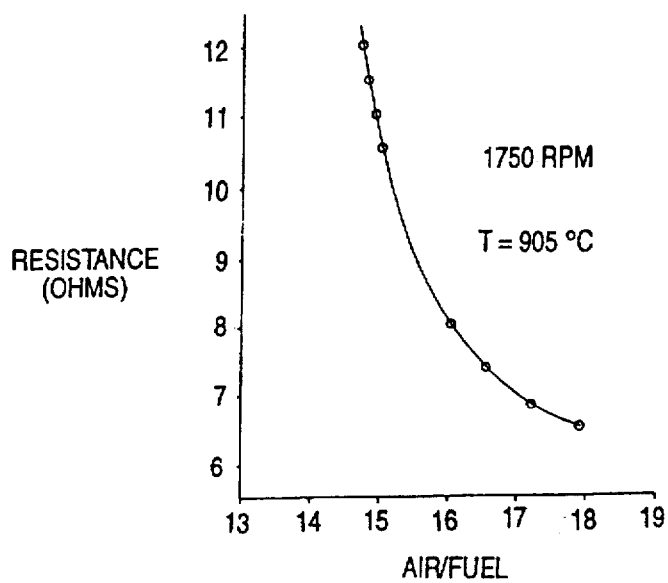
FIG. 4 is a graph of the resistance (ohms) vs. Air-to-Fuel ratio for a CoO oxygen sensor according to prior art.

As an example, the sensing material may be cobalt, which can convert to cobalt oxide (CoO or $Co_3O_4$) depending on the temperature and partial pressure of the oxygen. That is, as seen in FIG. 2, the particular phase of the Co-O material depends on the temperature and partial oxygen pressure to which the material is exposed. FIG. 2 shows a part of the $P_{O2}$-T phase diagram for this system, the solid and the dotted lines separate the Co, CoO, and $Co_3O_4$ phases. For (T, $P_{O2}$) pairs corresponding to the left of the solid line, the sensing material exists only as metallic cobalt. Between the solid and the dotted lines, the material exists as CoO; whereas, to the right of the dotted line, the material exists only as $Co_3O_4$. On the solid and dotted lines the material is a mixture of the two adjacent phases.

In the present invention, the sensing material may be present in bulk form or as a layer on a substrate, wherein for example the substrate is planar. The layer may be one having a longer length than width. The substrate may be selected from any suitable material, electrically insulating or non-insulating, which will be dependent on the particular use of the sensor as will be described in further detail below.

Figure 5:
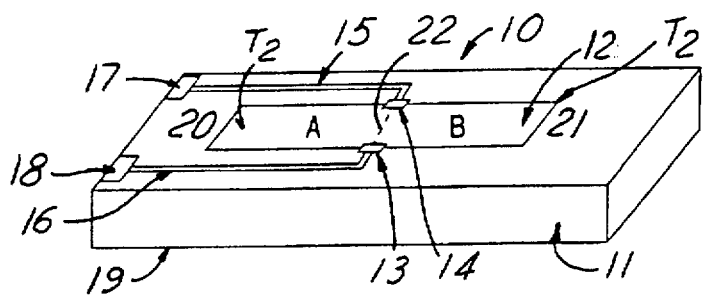
FIG. 5 is a schematic of an embodiment of an oxygen sensor according to the present invention where the measured physical property of the sensing material is its electrical resistivity.

FIG. 5 shows an embodiment of the present invention oxygen sensor 10 which is based on resistance measurement. A layer 12 of the metal (e.g. Co) or the metal oxide (CoO) is deposited on an electrically insulating substrate 11. The layer 12 in this embodiment is longer than it is wide. If electrical resistance of the layer is the property being monitored, then the substrate must be electrically insulating. Substrate 11 can be one of many materials known in the art such as alumina, silica, sapphire, and silicon nitride. Still others will be apparent in view of the present disclosure. Layer 12 can be deposited by one of many methods known in the art such as sputtering, electron-beam evaporation, laser ablation, chemical vapor deposition, sol-gel techniques, and thick film printing. Generally, this layer would preferably be a few microns thick. Thin layers minimize sensor response time limitations arising from the need of $P_{O2}$-related lattice defects in the material (e.g., Co ions in CoO, or O vacancies in $TiO_2$) to diffuse throughout the entire layer. On the other hand, thick layers tend to increase the longevity of the sensors. The sensing material of the present invention preferably has a density which is at least 60% of theoretical. If the layer is relatively thin (a few microns or less), 100% density is acceptable. If the layer is thick (e.g., several tens of microns or more) substantial porosity and small grain size (e.g., a few microns) are generally needed in order to decrease the distance over which the ions need to diffuse and thus to decrease the sensor response. Preferably, the sensing material has an average particle diameter less than 10 microns.

We found that it is critical to the present invention that the sensor also includes a heating means, connectable to a power source, so that a temperature gradient is maintained across the sensing material during its operation. As disclosed above, during the active sensing operation, according to the present invention, the sensing material exists in at least two of the materials phases defining a boundary line therebetween generally perpendicular to the longitudinal axis of the temperature gradient. This temperature gradient is necessary in order to maintain the presence of the at least two different phases, which may be, e.g., cobalt metal and cobalt oxide, or two forms of cobalt oxide in the material. The material may exist in more than two separate phases during operation, for example for a Co-O material, the concurrent phases may be Co/CoO/$Co_3O_4$, with boundary lines between adjacent two phases. It is to be understood in this invention, that these phases exist at different places in the material with contact between the phases being only at the boundary line between phases. That is, these phases are not intermingled at locations in the material as will be further explained and understood from the figures. For example, in FIG. 5, the phases are designated A and B with boundary line 22 therebetween. These phases are kept separate from one another by means of the use of the heating means which critically maintains a temperature gradient across the sensing material. When the partial pressure of oxygen changes in the ambient atmosphere to which the material is exposed, phase formation takes place. One phase increases in size and the other correspondingly decreases in size. Hence, the boundary line traverses along the longitudinal axis of the temperature gradient in response to the change in the oxygen partial pressure. For example, according to one aspect, if there are two phases present, CoO and $Co_3O_4$, as the sensor is exposed to changes in oxygen partial pressure, one of the phase increases in size and the other correspondingly decreases so that the boundary line between the phases moves to a different location on the sensing material.

When materials such as cobalt change from one phase to another phase, there is an associated hysteresis effect. This hysteresis effect is usually associated with the nucleation process required for phase transformation, i.e., the initial formation of critical size nuclei of the new phase. Thus in a system wherein the material is in one phase and then changes to another phase, hysteresis would result in a delay of formation of the new phase until critical size nuclei of the new phase form. The length of delay would be tied to the particular material. However, by maintaining a temperature gradient across the material the material is maintained in at least two forms in the material and slow response time associated with hysteresis can be avoided. In operation, it may be desirable to expose the sensor comprised of a metal like cobalt to oxygen to initiate formation of an oxide phase or phases prior to actual operation of the sensor, i.e., to pre-condition the sensor, e.g., prior to insertion in an automotive exhaust gas system as described in more detail below. This may be done, e.g., by exposing the deposited material to a temperature distribution in the range 700°–1000° C. in air.

The sensor would also include a means for furnishing an output signal in response to the traversal of the boundary line across a fixed detecting location of the sensing material. Since the phase change has associated therewith a change in a measurable physical property, the furnishing means detects the change in the physical property of the material at the fixed detecting location and hence the traversal of the boundary line past this fixed detecting location. Optimally this detecting location on the sensing material is of limited small size and optimally generally centrally located along the longitudinal axis of the temperature gradient and in some detecting embodiments, perpendicular thereto. While it is preferred that the detecting location is centrally located, it is only necessary that the detecting location not be at the ends near the extremes of the temperature gradient. Exemplary of these measurable physical properties are electrical resistivity, optical absorption, and mass. Still other will be apparent to those skilled in the art in view of the present disclosure.

Figure 5A:
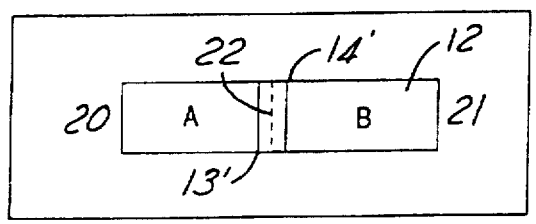
FIGS. 5A, 5B, & 5C are schematics of alternate embodiments of a portion of a FIG. 5 type oxygen sensor wherein the positioning of the electrical contacts has been modified.
Figure 5B:
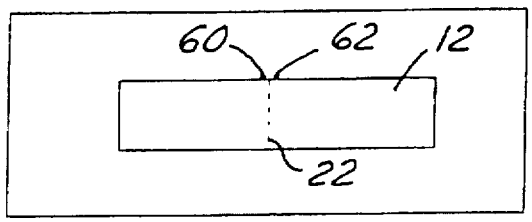
Figure 5C:
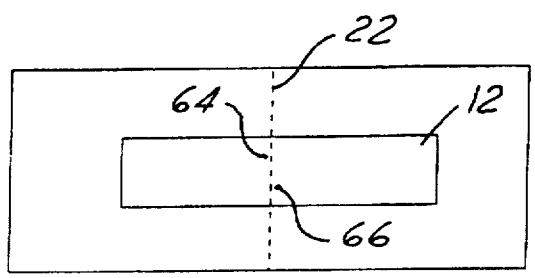

If desired to measure the phase change based on changes in electrical resistivity of the material resulting from changing oxygen partial pressure in the ambient atmosphere, it may be accomplished as shown in FIG. 5. In one embodiment of the present invention planar oxygen sensor, shown in FIG. 5, two electrical contacts 13 and 14 for resistance measurement are deposited on the two opposing narrow surfaces of material layer 12 along a line perpendicular to the length of the layer (which corresponds also to the longitudinal axis of the temperature gradient in this embodiment) and generally in the middle of the layer. These contacts 13 and 14 could alternately be deposited, e.g., as relatively closely spaced parallel strips 26 and 28 on one of the planar faces as shown in FIG. 5A, or one side as shown in FIG. 5B as 60 and 62, on the same planar face as shown in FIG. 5C as 64 and 66, or even as parallel strips (not shown), that is, one on one planar face and the other on an opposing planar face. The contacts could also be located within the sensing layer such that the region between the contacts would encompass the traversal of the boundary line during active sensing operation. Still other ways to detect the movement of the boundary line 22 associated with changes in oxygen partial pressure would be apparent to those skilled in the art in view of the present disclosure.

As would be appreciated by those skilled in the art in view of the present disclosure, the fixed detecting location defined by contacts 13 and 14 could be located at different places along the longitudinal axis of material 12 closer to either end of the material layer. Nearer the center ("generally centrally located") is however preferred because it is easier then to optimize sensor sensitivity and wide $P_{O2}$ range of operation as will be discussed later in this invention. Thus, by "generally centrally located" is meant that the detecting location is not at the ends of the sensing material at the extreme temperatures but located somewhere along the temperature gradient axis through which the boundary is expected to traverse during sensor operation. These contacts 13 and 14 in the configuration of FIG. 5 would optimally be generally along a line perpendicular to the temperature gradient axis, but this need not be exact. Electrical leads 15 and 16 are also deposited on the substrate 11 to connect contacts 13 and 14 to the electrical pads 17 and 18 where a voltage or a current is connected from an external source for the resistance measurement. Electrical contacts, leads and pads are made from a high temperature conductor such as platinum. These electrical means are able to furnish an output signal in response to the traversal of the boundary line corresponding to a phase change of the sensing material effected by the changing oxygen partial pressure of the sensing material in a region between the electrical means.

Further in this FIG. 5 embodiment, an electrical heater 19, made for example of platinum, is deposited on the back side of substrate 11 to raise the temperature of sensor 10 to the desired values. Heater 19 is constructed in such a way that it delivers different electrical power to different parts of the substrate so that a temperature gradient is established along the length of sensing material layer 12. The criticality of maintaining a temperature gradient across the sensing material has been discussed in detail previously. Consequently, the temperature $T_2$ at one end 20 of the sensing material layer is higher than the temperature $T_1$, at the other end 21 of layer 12. The temperature of the two contacts 13 and 14 can be measured and controlled with any temperature sensing element, many being well known in the art. For example, a thermistor can be deposited on the substrate 11 near contacts 13 and 14. If needed, more temperature sensing elements can be deposited on substrate 11 to better monitor and control the temperature gradient across sensor layer 12.

During the operation of invention oxygen sensor 10 for measuring a specific partial oxygen pressure $P_{O2,c}$, the power to heater 19 is adjusted so that the temperature $T_m$ at the two electrical contacts 13 and 14 is equal to $T_c$, the temperature which corresponds to the transition from one oxide phase to the other at the oxygen partial pressure $P_{O2,c}$. For a range of $P_{O2}$ around $P_{O2,c}$, sensing material layer 12 contains at least two distinct phase sections, such as metal oxide phases A and B, e.g. CoO and $Co_3O_4$, respectively, one to the left of and another to the right of the boundary line 22, which is seen as the division or separation of the two phases. This boundary line 22 is generally perpendicular to the temperature gradient (in this embodiment, perpendicular to the longitudinal axis of material layer 12). As can be seen from FIG. 5, these phases A and B exist concurrently, i.e., at the same time, in the material but at distinct places in the sensing material.

Figure 6:
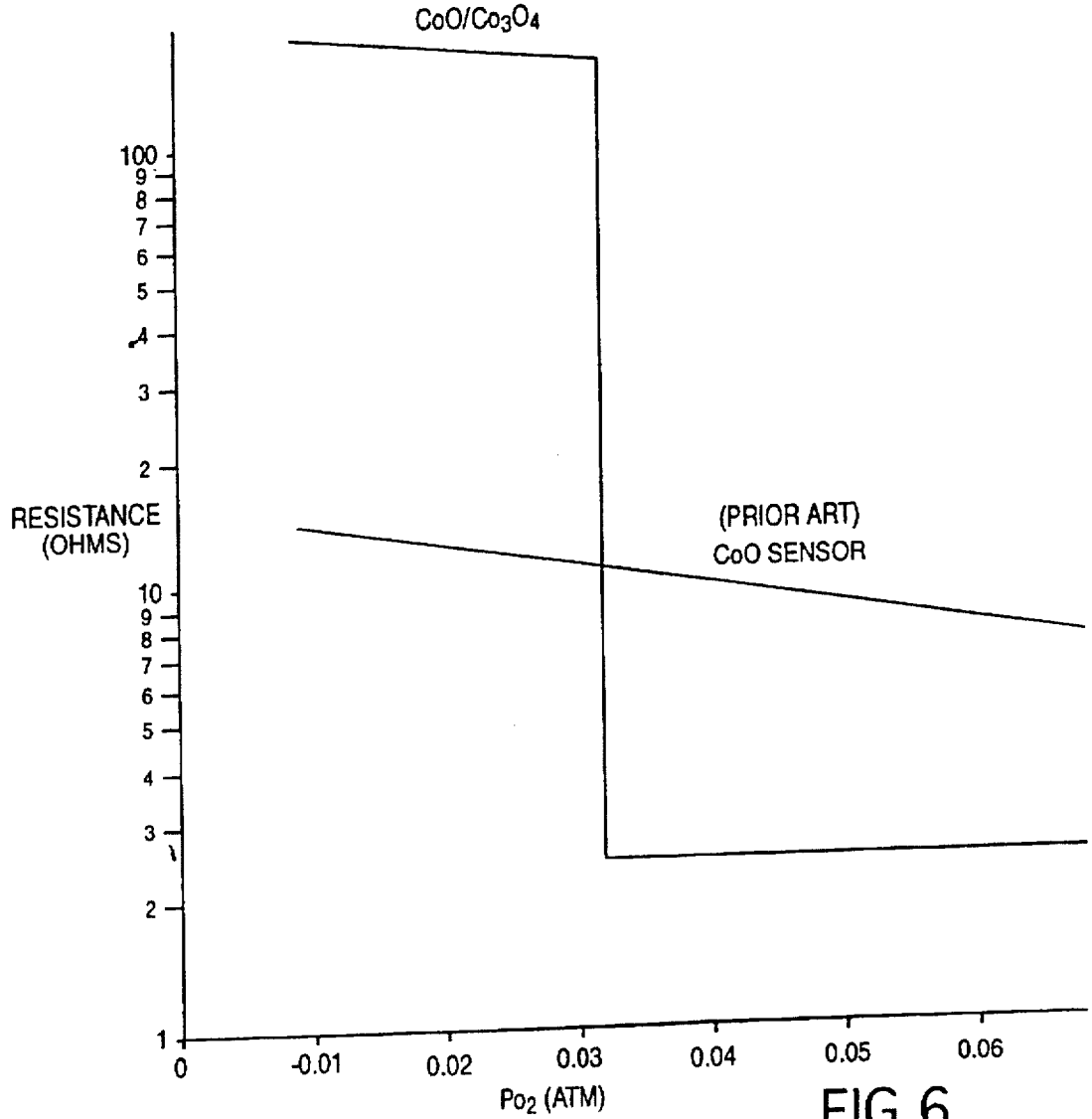
FIG. 6 is a graph showing the resistance (ohms) response of the FIG. 5 sensor to varying $P_{O2}$ or $O_2$ concentration. The resistance response of a FIG. 4 prior art CoO sensor is also shown for comparison.

In the case of $T_2$ being higher than $T_1$, and if the oxygen partial pressure increases, the boundary line 22 will move to the left as more of phase B ($Co_3O_4$) forms. If the resistance between contacts 13 and 14 is monitored, the resistance shows a large jump as the boundary line 22 passes by the two contacts which happens whenever the ambient $P_{O2}$ is varied through the value $P_{O2,c}$. This jump is shown in FIG. 6 for the $CoO/Co_3O_4$ system. In this example, the T-gradient along the layer is constant with $T_1$=860°C. and $T_2$=900° C. Hysteresis is avoided in this case because the two phases always are present and the nucleation of the new phase is not needed. It is apparent that, a different value of $P_{O2,c}$ can be detected by choosing another appropriate temperature at the position of the contacts 13 and 14.

The resistance of the sensing element between contacts 13 and 14 can be measured by methods well known in the art. For example, a current can be sent through contacts 13 and 14 and the measured voltage drop between these contacts can be used to calculate the resistance of the sensing material between these contacts; or a voltage can be applied to the sensing material element through a voltage divider circuit;

or the resistance between 13 and 14 can be one leg of a conventional resistance bridge. Still other configuration may be used as would be apparent to those skilled in the art in view of the present disclosure. For example, two additional contacts can be deposited one on each end of the sensing material and used to apply a voltage or the current. Contacts 13 and 14 are then used only to measure the voltage drop across them. The contacts 13 and 14 in this later embodiment would have to be offset relative to one another, i.e., not along the same perpendicular to the temperature gradient.

The type and magnitude of the temperature gradient in the sensor 10 depends on the application. In general, the smaller is the T-gradient, the higher is the accuracy of the sensor. If the T-gradient is constant along the sensing material layer 12, a smaller T-gradient means that the difference between $T_1$ and $T_2$ is smaller. In that case, the range of allowable variation of $P_{O2}$ that preserves both phases in the layer is smaller. A typical $P_{O2}$ range is one that covers an order of magnitude, that is the ratio of the maximum and minimum $P_{O2}$ is 10. The temperatures $T_1$ and $T_2$ at the two ends of layer 12 corresponding to these maximum and minimum $P_{O2}$ can be determined from the T-$P_{O2}$ phase diagram (e.g., FIG. 2 for Co-O system). If, during sensor operation, the ambient $P_{O2}$ unexpectedly changes to a value outside the allowable $P_{O2}$ range, the material may become a single phase, i.e., so that one of the other two phases in sensing layer 12 disappears and the sensor is not able to actively sense. In this case, when the ambient $P_{O2}$ returns to a normal value within the allowable $P_{O2}$ range, the sensor needs some extra time for the second phase to again form. Nevertheless, after this delay, the sensor will become fully operational and return to active sensing. A high accuracy around the desired value $P_{O2,c}$ combined with a wide range of allowable $P_{O2}$ may be achieved by generating a special non-constant T-gradient along sensing material layer 12. For example, the heater and the structure can be designed so that the T-gradient is small near the center of layer 12 and very large at the two ends of layer 12. From this discussion, it is apparent that the center of layer 12 is a convenient location for the contact pads 13 and 14.

Figure 1:
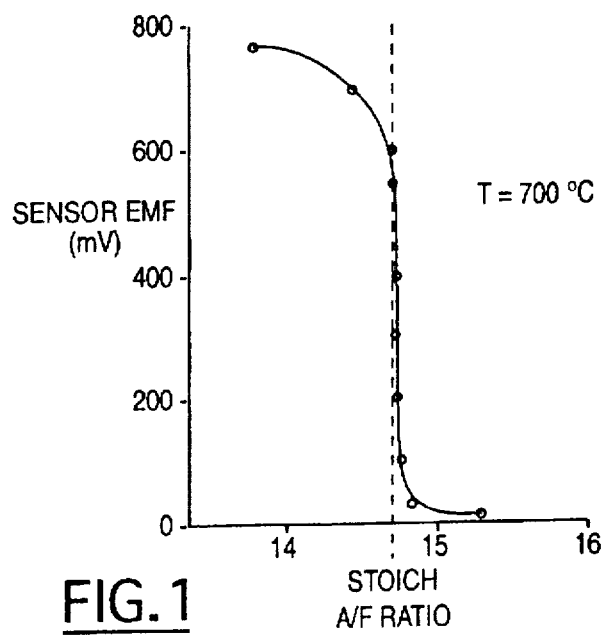
FIG. 1 is a graph showing the measured emf of a conventional automotive $ZrO_2$ oxygen sensor (lambda-sensor-type) as a function of the Air-to-Fuel Ratio of an engine.

The '182 patent sensor, as well as the present invention disclosed herein, can not be conveniently used to measure any value of a varying ambient oxygen pressure. Instead these sensors can monitor whether the ambient oxygen pressure is higher or lower than a selected specific value $P_{O2,c}$ (FIG. 6). In this respect, the sensor of this invention behaves similarly to the lambda sensor of the prior art (FIG. 1) used for stoichiometric A/F control, except that the "switch point" of the present sensor can be adjusted to be at any A/F value. That is, a new value of $P_{O2,c}$ or of $(A/F)_c$ can be selected by changing the temperature of layer 12 at the location of contacts 13 and 14 to the appropriate value.

Consequently, when the present sensor is used as an oxygen or A/F feedback control sensor, the feedback control is of the "limit-cycle" type rather than proportional control, similar to the stoichiometric A/F control systems based on the lambda sensor. In this limit-cycle control, the A/F ratio is ramped from a value lower than $(A/F)_c$, to a value higher than $(A/F)_c$, or vice versa, with the direction of the ramping depending on the sensor output. When A/F passes through $(A/F)_c$, the sensor signal changes from a low to a high value or from a high to a low value as the boundary line 22 traverses (FIG. 5), correspondingly from the left to the right or right to left, and the electronic feedback system is ordered to change direction of the A/F sweep.

Consequently, the A/F oscillates between two A/F values, one lower and the other higher than $(A/F)_c$, at a certain frequency called "limit-cycle frequency".

The device of the present invention can be made in planar configurations other than the one shown in FIG. 5. For example, a planar structure can be fabricated similarly to the so-called planar $ZrO_2$ sensors, both the stoichiometric Nernst-type and $O_2$-pumping-based UEGO and LEGO sensors. In these sensors, a series of ceramic tapes made from $ZrO_2$ (and possibly also from other materials) having appropriate geometry (shape and thickness) together with planar heater and electrodes are pressed together and sintered at high temperatures to form the planar sensor element.

Although planar geometry is a most convenient geometry for establishing a temperature gradient, more 3-dimensional embodiments can also be used. Also temperature distributions other than along a length of the sensing material, as shown e.g., along the length of the sensing material layer of the embodiment of FIG. 5, may be used. Such other distributions are acceptable as long as they are such that both phases of the sensing material exist, during active sensing operation, in the sensing material separated by a phase boundary line which moves through the detecting location, in the FIG. 5 embodiment being defined by spaced contacts 13 and 14 which detect the transversal of the phase boundary line. These embodiments as well as others included within the present invention will be apparent to those skilled in the art in view of the present disclosure.

Figure 7:
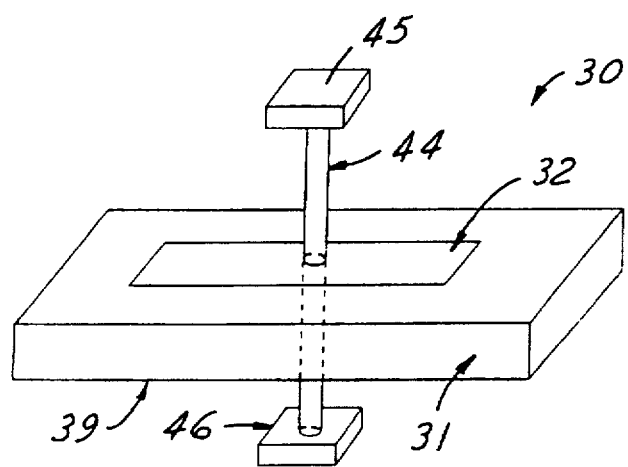
FIG. 7 is a schematic of an embodiment of an oxygen sensor according to the present invention where the measured physical property of the sensing material is its optical absorption.

FIG. 7 shows another embodiment 30 according to the present invention where the changing physical property of the sensing material being measured is its optical absorption. Embodiment 30 is similar to embodiment 10 except that electrical leads, pads, and contacts (used therein for measuring electrical resistance) are not needed in this embodiment 30 for operation of a sensor based on changing optical absorption. To measure the changing optical absorption, at some fixed detecting small area of the sensing material through which the phase boundary transverses, a small size circular or rectangular light beam 44 of the proper wavelength from a light source 45 is directed upon and through this small area of the sensing material layer 32 preferably near the center of layer 32. The light transmitted through the sensing material layer 32 and the substrate 31 is detected with a light detector 46. In this embodiment, substrate 31 must be transparent to the light beam 46 but the substrate does not have to be electrically insulating as with the first (resistivity measuring) embodiment described above. However, if the heating means 39 for providing the temperature gradient across the layer comprises a metal coating, e.g., a printed metallic coating as might be used as heating means 19 in the prior FIG. 5 embodiment above, it would still be necessary to provide an electrically insulating substrate. It is also desirable that the heating means 39 does not interfere with the optical detection of the associated sensor material phase change.

Limitations due to ion diffusion in the material (e.g. Co ions in the case of CoO) can be overcome by operating at sufficiently high temperatures where the diffusion process is fast; and by using ceramics with high porosity and very small grain size or by using thin films. Limitations in the speed of this phase change due to slow surface processes affecting the transfer of oxygen between the material and the ambient gas can be minimized by, again, operating at high temperatures or by adding on the surface of the materials catalytic particles (e.g., Pt) which help the oxygen transfer.

Advantageously, according to the present invention, the limitations due to the nucleation process can be minimized by operating the sensor so that both phases are always present in the sensing material. This is accomplished by establishing a temperature distribution along the material instead of maintaining the material at a constant temperature as in prior art sensors.

Various preferred embodiments of the invention have now been described in detail. In addition, however, many changes and modifications can be made to these embodiment without departing from the nature and spirit of the invention. Accordingly, it is to be understood that the invention is not limited to these details but is defined by the appended claims.

What is claimed is:

1. An oxygen sensor for detecting a change of oxygen partial pressure in an ambient atmosphere through a change of a measurable physical property of a sensing material, said sensor comprising:

a sensing material being selected from metal or its oxides and which, when at an elevated temperature and exposed to a gas containing a changing partial pressure of oxygen, is capable of changing from one metal or metal oxide phase to another such oxide phase and vice versa and associated therewith a change in a measurable physical property thereof;

heating means connectable to a power source able to maintain a temperature gradient across said sensing material whereby said material exists, during active sensing operation, in at least two of said phases defining a boundary line therebetween generally perpendicular to the longitudinal axis of said temperature gradient, said boundary line traversing longitudinally along said axis in response to changes in the oxygen partial pressure of the ambient atmosphere; and means for furnishing an output signal in response to traversal of said boundary line across a fixed detecting location of the sensing material.

2. The sensor according to claim 1 wherein said physical property is selected from the group consisting of electrical resistance, mass, and optical absorption.

3. The sensor according to claim 1 wherein said heating means comprise an electrically conductive material located in proximate location to said sensing material and being connectable to said power source for maintaining said temperature gradient.

4. The sensor according to claim 1 wherein said sensing material has an average particle diameter of less than 10 microns.

5. The sensor according to claim 1 wherein the maximum difference in temperatures across the sensing material provided by said heating means during sensing operation corresponds to a ratio of the maximum to the minimum $P_{o2}$ in the ambient during sensing equal to 10.

6. The sensor according to claim 1 where said ambient atmosphere is an automotive exhaust gas.

7. The sensor according to claim 1 wherein the traversal of said boundary line is detected through a change of optical absorption of said material, wherein said furnishing means comprises:

a light source providing a light beam onto said sensing material in said fixed detecting location and a light detector in a position to detect the amount of light transmitted through the sensing material.

8. The sensor according to claim 1 wherein said fixed detecting location is centrally located along longitudinal axis of said temperature gradient.

9. The sensor according to claim 1 wherein said traversal of said boundary line is detected through a change of electric resistance of said material, wherein said furnishing means comprises:

spaced apart electrical means located within or on the same or opposing surfaces of said sensing material for measuring the electrical conductivity of said sensing material therebetween, for furnishing an output signal in response to the traversal of said boundary line between said electrical means.

10. The sensor according to claim 9 wherein said heating means comprises an electrically conductive material (a) electrically insulated from said sensing material, (b) located in proximate location to said sensing material, (c) and being connected to said power source for maintaining said temperature gradient.

11. The sensor according to claim 6 wherein said electrical means are affixed to the same or opposing sides of said sensing material.

12. The sensor according to claim 1 wherein said sensing material is a layer deposited on a substrate.

13. The sensor according to claim 12 wherein said substrate is planar.

14. The sensor according to claim 1 wherein said sensing material is selected from a metal, a compound of two or more metals, or oxides thereof.

15. The sensor according to claim 14 wherein said metal is selected from the group consisting of copper, palladium, indium, ruthenium, and rhodium, 3d transition metals, and rare earth elements.

16. The sensor according to claim 1 wherein said sensing material is present in at least two of said phases defining a boundary line therebetween perpendicular to the axis of the temperature gradient of said material.

17. The sensor according to claim 16 wherein said sensing material is present in two oxide phases defining a boundary line therebetween perpendicular to the axis of the temperature gradient of said material.

18. The sensor according to claim 17 wherein said phases comprise two oxides of cobalt: $CoO$ and $Co_3O_4$.

* * * * *